US009457102B2

(12) United States Patent
Negishi et al.

(10) Patent No.: US 9,457,102 B2
(45) Date of Patent: Oct. 4, 2016

(54) THERAPEUTIC MUSCULAR DYSTROPHY DRUG HAVING BUBBLE LIPOSOME LOADED WITH MORPHOLINO AS ACTIVE INGREDIENT

(75) Inventors: Yoichi Negishi, Hachioji (JP); Yoko Takahashi, Hachioji (JP); Kazuo Maruyama, Itabashi-ku (JP); Yukihiko Aramaki, Hachioji (JP)

(73) Assignee: NEPA GENE CO., LTD., Ichikawa-shi (JP)

( * ) Notice: Subject to any disclaimer, the term of this patent is extended or adjusted under 35 U.S.C. 154(b) by 106 days.

(21) Appl. No.: 14/116,316

(22) PCT Filed: Apr. 25, 2012

(86) PCT No.: PCT/JP2012/061020

§ 371 (c)(1),
(2), (4) Date: Nov. 7, 2013

(87) PCT Pub. No.: WO2012/153635

PCT Pub. Date: Nov. 15, 2012

(65) Prior Publication Data

US 2014/0155813 A1 Jun. 5, 2014

(30) Foreign Application Priority Data

May 9, 2011 (JP) ................................ 2011-104300

(51) Int. Cl.

| | |
|---|---|
| ***A61K 47/48*** | (2006.01) |
| ***A61K 41/00*** | (2006.01) |
| ***A61K 9/00*** | (2006.01) |
| ***A61K 47/24*** | (2006.01) |
| ***A61K 9/127*** | (2006.01) |
| ***C12N 15/88*** | (2006.01) |
| ***C12N 15/113*** | (2010.01) |

(52) U.S. Cl.

CPC ....... *A61K 47/48815* (2013.01); *A61K 9/0019* (2013.01); *A61K 9/1271* (2013.01); *A61K 41/0028* (2013.01); *A61K 41/0047* (2013.01); *A61K 47/24* (2013.01); *C12N 15/113* (2013.01); *C12N 15/88* (2013.01); *C12N 2310/11* (2013.01); *C12N 2310/3233* (2013.01); *C12N 2310/3515* (2013.01); *C12N 2320/32* (2013.01); *C12N 2320/33* (2013.01)

(58) Field of Classification Search

None

See application file for complete search history.

(56) References Cited

U.S. PATENT DOCUMENTS

| | | | |
|---|---|---|---|
| 6,365,351 B1 | 4/2002 | Iversen | |
| 7,094,765 B1 | 8/2006 | Iversen et al. | |
| 2001/0024783 A1 | 9/2001 | Iversen | |
| 2003/0171328 A1 | 9/2003 | Iversen | |
| 2006/0099616 A1 | 5/2006 | Van Ommen et al. | |
| 2006/0147952 A1 | 7/2006 | Van Ommen et al. | |
| 2006/0269587 A1 | 11/2006 | Iversen et al. | |
| 2007/0207194 A1* | 9/2007 | Grayburn ............. | A61K 9/0019 424/450 |
| 2009/0076246 A1 | 3/2009 | Van Deutekom | |
| 2011/0294753 A1 | 12/2011 | De Kimpe et al. | |
| 2011/0312086 A1 | 12/2011 | Van Deutekom | |

FOREIGN PATENT DOCUMENTS

| | | |
|---|---|---|
| JP | 2001 57207 | 6/2001 |
| JP | 2001-507207 | 6/2001 |
| JP | 2002-537230 | 11/2002 |
| JP | 2002 537230 | 11/2002 |
| JP | 2006-523101 | 10/2006 |
| JP | 2006 523101 | 10/2006 |
| JP | 2011 502118 | 1/2011 |
| JP | 2011-502118 | 1/2011 |
| WO | WO 97/40679 A1 | 11/1997 |
| WO | WO 00/44897 A1 | 8/2000 |
| WO | WO 2004/083446 A2 | 9/2004 |
| WO | WO 2009/054725 A2 | 4/2009 |

OTHER PUBLICATIONS

Jearawiriyapaisarn, et al. (2008) "Sustained Dystrophin Expression Induced by Peptide-conjugated Morpholino Oligomers in the Muscles of mdx Mice", Molecular Therapy, 16(9): 1624-29.*

Lu, et al. (2003) "Microbubble ultrasound improves the efficiency of gene transduction in skeletal muscle in vivo with reduced tissue damage", Gene Therapy, 10(5): 396-405.*

Kodama, et al. (2010) "Evaluation of Transfection Efficiency in Skeletal Muscle Using Nano/Microbubbles and Ultrasound", Ultrasound in Medicine & Biology, 36(7): 1196-205.*

Ishii, Y., et al. "Development of Gene Delivery System into Skeletal Muscles by Bubble Liposomes and Ultrasound", Abstracts of 131st Annual Meeting of Pharmaceutical society of Japan 4, pp. 232, (29P-0453),( Mar. 2011).

Sekine, S., et al., "Bubble Liposome to Choonpa Heiyo ni yoru Kekkan o Kaishita Kin Soshiki eno Idenshi Donyu Koka ni Tsuite", Journal of Pharmaceutical Science and Technology, Japan, vol. 68, No. suppl, p. 297, (Apr. 2008).

Endo, Y., et al., "Bubble Liposome ni yoru Mouse Keibu Kin Soshiki eno siRNA Sotatsu System no YuyoseivnoHyoka", Journal of Pharmaceuticl Science and Technology, Japan, vol. 68, No. Suppl, p. 299, (Apr. 2008).

(Continued)

*Primary Examiner* — Robert M Kelly

(74) *Attorney, Agent, or Firm* — Oblon, McClelland, Maier & Neustadt, L.L.P.

(57) ABSTRACT

To provide a technology for introducing a PMO with remarkably enhanced cell permeability, leading to significantly enhanced introduction efficiency to thereby provide a therapeutic drug that dramatically ameliorates a medical condition of DMD. Also provided is a therapeutic drug for Duchenne muscular dystrophy, including as an active ingredient a Bubble liposome having a specific morpholino oligomer (PMO) bound to a surface thereof, in which the PMO is introduced into a muscle fiber (muscle cell) of a muscle tissue with high efficiency by administration of the therapeutic drug into the muscle tissue or into a blood vessel followed by ultrasound irradiation to the muscle tissue transcutaneously.

5 Claims, 7 Drawing Sheets

(56) References Cited

OTHER PUBLICATIONS

Negishi, Y., et al., "Bubble liposome to choonpa Gijutsu o Yugo shita Kin Soshiki eno Idenshi Donyu System no Kaihatsu", Abstracts of $130^{th}$ annual Meeting of Pharmaceutical Society of Japan 1, pp. 235 (S19-1), (Mar. 2010).
Alter, J., et al., "Systemic delivery of morpholino oligonucleotide restores dystrophin expression bodywide and improves dystrophic pathology", Nature Medicine , vol. 12, No. 2, pp. 175-177, (Feb. 2006).
International Search Report Issued Jun. 5, 2012 in PCT/JP12/061020 Filed Apr. 25, 2012.
Office Action issued May 7, 2015 in Japanese Patent Application No. 2011-104300 (with English translation).
Julia Alter, Microbubble Stability is a Major Determinant of the Efficiency of Ultrasound and Microbubble Mediated in Vivo Gene Transfer, Ultrasound Med. Bio., vol. 35. No. 6, 2009, pp. 976-984.
Hans A. Heemskerk, et al., "In vivo comparison of 2'-0-methyl phosphorothioate and morpholino antisense oligonucleotides for Duchenne muscular dystrophy exon skipping", The Journal of Gene Medicine, 2009, 11(3): pp. 257-266.
Susan Fletcher, et al., "Dystrophin expression in the mdx mouse after localized and systemic administration of a morpholino antisense oligonucleotide", The Journal of Gene Medicine, 2006, 8, pp. 207-216.
Journal of Pharmaceutical Science and Technology, Japan, Apr. 30, 2008, vol. 68, No. Suppl., p. 297.
Journal of Pharmaceutical Science and Technology, Japan, Apr. 30, 2008, vol. 68, No. Suppl., p. 299.
Abstracts of the $130^{th}$ Annual Meeting of the Pharmaceutical Society of Japan, Development of Cellular and Gene Therapy Products for Bioactive Protein-Based Therapy, Mar. 5, 2010, p. 235 (S19-1).
Kazuo Maruyama, et al., Drug an Gene Delivery by "Bubble Liposomes" and Ultrasound, Yakugaku Zasshi 127(5), 2007, pp. 781-787 (with English abstract).
Abstract of the $26^{th}$ Annual Meeting of the Academy of Pharmaceutical Science and Technology , Japan, 2011, vol. $26^{th}$, p. 165 (30-5-07).

* cited by examiner

THERAPEUTIC MUSCULAR DYSTROPHY DRUG HAVING BUBBLE LIPOSOME LOADED WITH MORPHOLINO AS ACTIVE INGREDIENT

TECHNICAL FIELD

The present invention relates to a therapeutic drug for Duchenne muscular dystrophy, including as an active ingredient a Bubble liposome having a specific morpholino oligomer (PMO) bound to a surface thereof, in which the PMO is introduced into a muscle fiber (muscle cell) of a muscle tissue with high efficiency by administration of the therapeutic drug into the muscle tissue or into a blood vessel followed by ultrasound irradiation to the muscle tissue transcutaneously.

BACKGROUND ART

Muscular dystrophies are X-linked recessive genetic diseases that exhibit muscle fiber degeneration and necrosis as main lesions and cause progressive muscular atrophy.

Duchenne muscular dystrophy (DMD) and Becker muscular dystrophy (BMD) are known as the muscular dystrophies.

In particular, "DMD" is a disease that has a high incidence and exhibits severe symptoms. DMD is caused by a deficiency in dystrophin protein due to introduction of a stop codon into an exon of a dystrophin gene by a point mutation or a frame shift mutation.

DMD has an incidence of 1 in 3,500 newborn males. DMD patients show the following clinical symptoms: onset of the disease during early childhood; a loss of ambulation at around 10 years of age; and development of a medical condition leading to death by respiratory failure or heart failure in their 20s. Therefore, it is rare that the DMD patients survive beyond their 30s.

It should be noted that "BMD" is a disease due to a mutation that does not produce a stop codon, and occurs when the dystrophin protein itself is expressed but its structure is abnormal. Symptoms of BMD are milder and less progressive than those of DMD.

Under the present circumstances, there is no effective therapeutic method for such severe DMD. In recent years, however, usefulness of an antisense nucleic acid constructed of a morpholino oligomer (PMO) has attracted attention (see Non Patent Literature 1 and Patent Literature 1).

A therapy using an antisense nucleic acid is a technology involving administering an oligomer having a sequence complementary to a target splicing site to induce sequence-specific exon skipping (read-through of a stop codon resulting from a mutation on an exon) in the dystrophin gene and restore the protein expression.

In addition, when the PMO is used as the antisense nucleic acid, there is an advantage in that the PMO is a very stable substance that is hardly degraded in vivo unlike a normal RNA-based oligomer.

The PMO is a technology that has attracted attention in a therapy for DMD as described above, but has a crucial problem in its clinical use.

The PMO shows extremely low cell permeability. Hence, in order to achieve the clinical application, it is essential to develop means for allowing passage of the PMO through capillary walls, which are present in large amounts in a muscle tissue, to significantly improve introduction efficiency of the PMO into muscle fibers (muscle cells).

At the present stage, a systemic therapy via intravascular administration of the PMO cannot be performed, and thus it is necessary to continuously perform local intramuscular administration, resulting in remarkable reductions in QOL of the patients.

Further, under the present circumstances, the PMO cannot be introduced into muscle fibers (muscle cells) of the heart and diaphragm, which cause heart failure and respiratory distress as immediate causes of death from DMD, respectively.

CITATION LIST

Patent Literature

[PTL 1] JP 2011-502118 W

Non Patent Literature

[NPL 1] J. Alter et al, Nat. Med., 2006

SUMMARY OF INVENTION

Technical Problem

The present invention has been made to solve the above-mentioned problems, and an object of the present invention is to provide a technology for introducing a PMO with remarkably enhanced cell permeability, leading to significantly enhanced introduction efficiency.

Thus, another object of the present invention is to provide a therapeutic drug that dramatically ameliorates a medical condition of DMD.

Solution to Problem

The inventors of the present invention have made extensive studies. As a result, the inventors have found that administration of a Bubble liposome having a PMO bound to a surface thereof and ultrasound irradiation to a muscle tissue transcutenously allow the PMO to be introduced into a muscle fiber (muscle cell) of the muscle tissue with extremely high efficiency, and allow a dystrophin deficiency in a DMD disease to be remarkably restored.

The inventors have also found that intravascular administration of the Bubble liposome enables to restore dystrophin deficiency of DMD in muscle fibers (muscle cells) of skeletal muscles of the whole body and muscle tissues of the heart and diaphragm (allows a systemic therapy to be performed).

The present invention has been made based on these findings. That is, the present invention according to a first aspect relates to a therapeutic drug for Duchenne muscular dystrophy, including as an active ingredient a Bubble liposome having a morpholino oligomer that has the following properties (A1) to (A3) bound to a surface thereof:

(A1) a morpholino oligomer having a function of, in a splicing process for pre-mRNA of a dystrophin gene having a stop codon resulting from a mutation, producing mature mRNA in which an exon having the mutation is skipped;

(A2) a morpholino oligomer formed of a complementary base sequence to a region including a splicing enhancer sequence of the exon; and (A3) a morpholino oligomer having a polymerization degree of 15 to 50 mer, in which the therapeutic drug is used according to the following usage (B):

(B) a usage in which the morpholino oligomer is introduced into a muscle cell of a muscle tissue with high efficiency by administration of a Bubble liposome having the morpholino oligomer bound to a surface thereof into the muscle tissue or into a blood vessel followed by irradiating the muscle tissue with ultrasound transcutaneously.

In addition, the present invention according to a second aspect relates to a therapeutic drug for muscular dystrophy according to the first aspect, in which the exon includes any one of exons 2, 8, 23, 43 to 46, and 50 to 53.

In addition, the present invention according to a third aspect relates to a therapeutic drug for muscular dystrophy according to the first or second aspect, in which the Bubble liposome is a PEG-liposome encapsulating a perfluorohydrocarbon, and has an average particle diameter of 50 to 500 nm.

In addition, the present invention according to a forth aspect relates to a therapeutic drug for muscular dystrophy according to any one of the first to third aspects, in which the administration includes systemic administration via a blood vessel.

In addition, the present invention according to a fifth aspect relates to a therapeutic drug for muscular dystrophy according to the forth aspect, in which the muscle tissue includes muscle tissues of heart and diaphragm.

In addition, the present invention according to a sixth aspect relates a therapeutic method for Duchenne muscular dystrophy, including using a therapeutic drug for Duchenne muscular dystrophy including as an active ingredient a Bubble liposome having a morpholino oligomer that has the following properties (A1) to (A3) bound to a surface thereof:

(A1) a morpholino oligomer having a function of, in a splicing process for pre-mRNA of a dystrophin gene having a stop codon resulting from a mutation, producing mature mRNA in which an exon having the mutation is skipped;

(A2) a morpholino oligomer formed of a complementary base sequence to a region including a splicing enhancer sequence of the exon; and (A3) a morpholino oligomer having a polymerization degree of 15 to 50 mer, in which the therapeutic drug is used according to the following usage (B):

(B) a usage in which the morpholino oligomer is introduced into a muscle cell of a muscle tissue with high efficiency by administration of a Bubble liposome having the morpholino oligomer bound to a surface thereof into the muscle tissue or into a blood vessel followed by irradiating the muscle tissue with ultrasound transcutaneously.

In addition, the present invention according to a seventh aspect relates to a therapeutic method for muscular dystrophy according to the sixth aspect, in which the exon includes any one of exons 2, 8, 23, 43 to 46, and 50 to 53.

In addition, the present invention according to an eighth aspect relates to a therapeutic method for muscular dystrophy according to the sixth or seventh aspect, in which the Bubble liposome is a PEG-liposome encapsulating a perfluorohydrocarbon, and has an average particle diameter of 50 to 500 nm.

In addition, the present invention according to a ninth aspect relates to a therapeutic method for muscular dystrophy according to any one of the sixth to eighth aspect, in which the administration includes systemic administration via a blood vessel.

In addition, the present invention according to a tenth aspect relates to a therapeutic method for muscular dystrophy according to the ninth aspect, in which the muscle tissue includes muscle tissues of heart and diaphragm.

Advantageous Effects of Invention

According to the present invention, the symptoms of DMD can be dramatically ameliorated by performing intravascular administration once in a therapy using a PMO, which has required continuous (frequent) local intramuscular administration heretofore. In addition, according to the present invention, the systemic therapy for DMD can be performed.

Further, according to the present invention, the symptoms of DMD can be ameliorated even in the muscle tissues of the heart and diaphragm (muscle tissues that cause heart failure and respiratory distress along with progression of DMD, respectively), which have been unable to be treated heretofore.

DESCRIPTION OF EMBODIMENTS

Hereinafter, embodiments of the present invention are described in detail.

The present invention relates to a therapeutic drug for Duchenne muscular dystrophy, including as an active ingredient a a Bubble liposome having a specific morpholino oligomer (PMO) bound to a surface thereof, in which the PMO is introduced into a muscle fiber (muscle cell) of a muscle tissue with high efficiency by administration of the therapeutic drug into the muscle tissue or into a blood vessel followed by irradiating the muscle tissue with ultrasound transcutaneously.

(Active Ingredient of Therapeutic Drug for DMD)

A medical condition that can be treated by the present invention is Duchenne muscular dystrophy (DMD).

Figure 1:
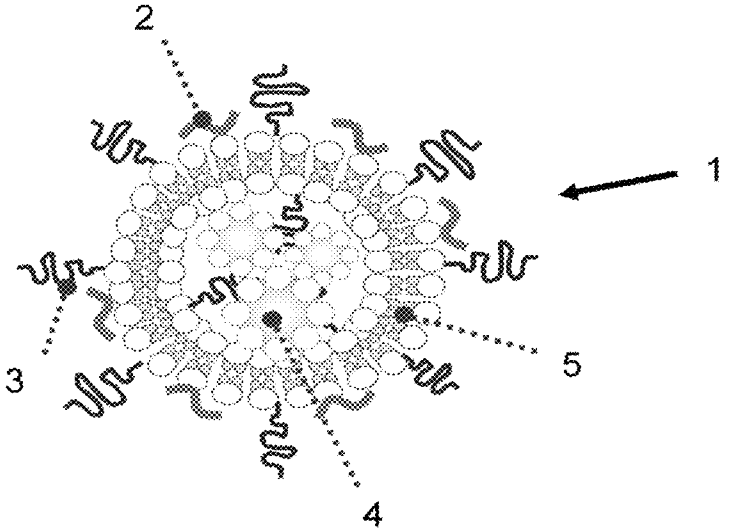
FIG. 1 is a view illustrating one aspect of a PMO-loaded Bubble liposome in the present invention.

The therapeutic drug for DMD of the present invention includes as an active ingredient "a Bubble liposome having a specific PMO bound to a surface thereof." It should be noted that, herein, the Bubble liposome is sometimes simply referred to as "PMO-loaded Bubble liposome." FIG. 1 illustrates one aspect of the PMO-loaded Bubble liposome.

Herein, the PMO refers to one bound to surfaces of the Bubble Liposomes, not one encapsulated into the Bubble liposomes.

It should be noted that, specifically, the binding in this case not only includes an electrical bond being charged, a hydrogen bond, a covalent bond, and the like but also includes a state in which the PMO is fitted in grooves formed by lipid molecules in the surfaces of the Bubble liposomes, and the like.

It should be noted that the PMO loading capacity of the Bubble liposomes varies depending on, for example, lipid molecules constituting the liposomes, and for example, in the case of PEG-liposomes formed of neutral phospholipids, the PMO loading capacity is about 2 μmol or less, preferably about 1.7 μmol or less with respect to Bubble liposomes having a total lipid amount of 1 mg.

(Morpholino Oligomer (PMO))

The 'morpholino oligomer' (phosphorodiamidate morpholino oligomer; PMO) in the present invention refers to an oligomer obtained by polymerizing morpholino subunits (monomers).

Figure 2:
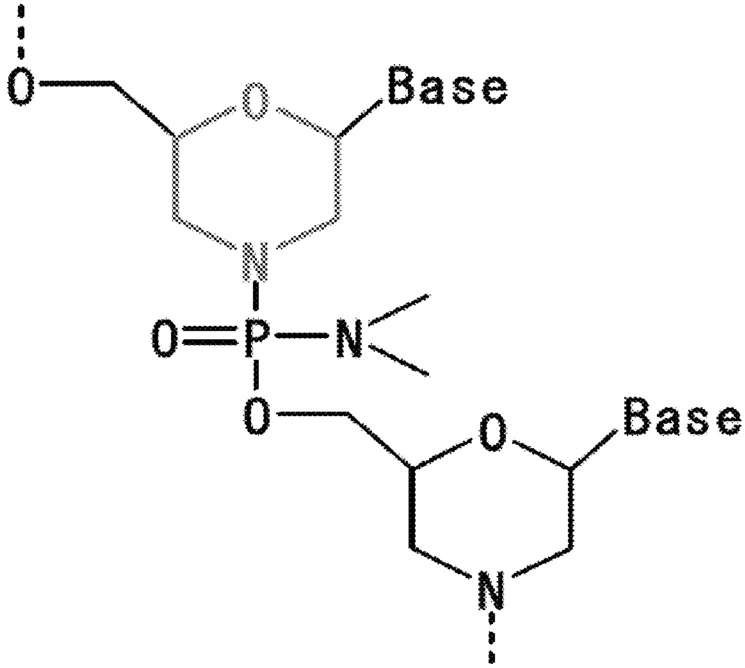
FIG. 2 is a view illustrating a polymerization structure of morpholino constituent units.

The morpholino subunit is a nucleotide analog, and refers to one having a structure in which the entire ribose (constituent sugar) of a ribonucleotide as a constituent unit of RNA is replaced by a morpholino ring. For reference, FIG. 2 illustrates a view of a polymerization structure of the constituent units.

The PMO has a base sequence similarly to DNA or RNA and is a molecule that functions as an antisense nucleic acid.

Further, the PMO is a substance extremely stable in a living body or in nature because of being not degraded by RNase or the like, and hence may be used as a molecule effective for a therapy using an antisense nucleic acid.

The PMO in the present invention is a morpholino polymer polymerized so as to have a complementary (antisense) base sequence to a region including a 'splicing enhancer site' on a dystrophin gene in DMD patients (or DMD-affected animals).

It should be noted that the splicing enhancer site is a region that plays an important role in the excision of an intron from pre-mRNA by splicing. The site is present in both of an intron and an exon, but the site on the exon is a target of the present invention.

The PMO as the antisense nucleic acid inhibits the formation of a spliceosome complex to induce exon skipping in a sequence-specific manner by hybridization with the splicing enhancer site of pre-mRNA of a dystrophin gene.

Then, finally, in a splicing process, the exon of interest (exon that has a stop codon and causes DMD) is skipped to produce mature mRNA that enables the expression of a dystrophin protein.

Figure 3:
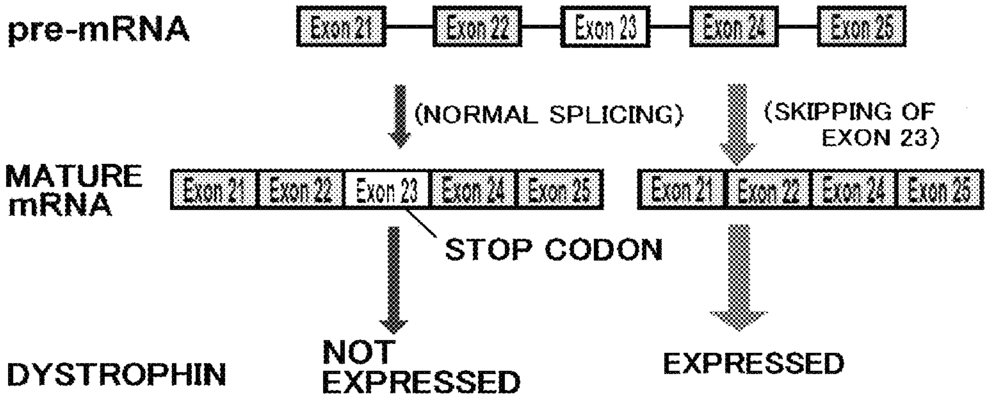
FIG. 3 is a view illustrating a mechanism in which PMO introduction induces exon skipping in exon 23 of a dystrophin gene that causes DMD.

It should be noted that FIG. 3 illustrates one aspect of mechanisms of the exon skipping.

Specific examples of the exon that causes DMD may include exons 2, 8, 23, 43 to 46, and 50 to 53 in a human dystrophin gene. In particular, exons 23, 46, 50, and 51 may be given. In this connection, a CDS sequence of the human dystrophin gene is set forth in SEQ ID NO: 9 of the sequence listing.

Further, specific examples of the antisense PMO (PMO having a sequence complementary to a region including a splicing enhancer site of the exon that causes DMD) may include PMOs comprising a base sequences set forth in SEQ ID NO: 1 (corresponding to exon 46), SEQ ID NO: 2 (corresponding to exon 50), and SEQ ID NO: 3 (corresponding to exon 51).

It should be noted that those molecular species are "PMOs" and hence there is no molecular species that can be set forth in the sequence listing. Thus, the PMO (morpholino oligomer having an antisense sequence) of the present invention is described by referring to information on the base sequences set forth in SEQ ID NOS: 1 to 3 as "DNAs."

Further, when the present invention is applied to any other mammal animal than a human, an exon that causes DMD in a dystrophin gene (gene having an ortholog relationship with SEQ ID NO: 9 above) of the animal is a target of the skipping.

For example, in the case of an mdx mutant mouse, a mutation that causes DMD is present in exon 23, and hence an antisense PMO having a function of skipping the exon may be used. Specific examples thereof may include a PMO comprising a base sequence set forth in SEQ ID NO: 4.

The polymerization degree of the PMO may be, for example, 15 to 50 mer. It should be noted that PMO with higher polymerization degree is desirable from the viewpoint of specificity, and the polymerization degree is preferably 18 mer or more, particularly preferably 20 mer or more, more particularly preferably 22 mer or more.

Further, PMO with lower polymerization degree is preferred from the viewpoint of introduction efficiency, and the polymerization degree is suitably 40 mer or less, more suitably 30 mer or less.

It should be noted that the PMO of the present invention may have a modification molecule bound to its 3' side and/or 5' side. For example, a PMO bound to a labeling molecule such as a fluorescent substance or an antigen substance may be used.

(Bubble Liposomes)

The 'Bubble liposomes' in the present invention refer to liposomes having a nano particle size and encapsulating a perfluorohydrocarbon (ultrasound contrast agent).

The liposomes have only to be miniaturized products obtained by passing liposomes having a large particle diameter, which are prepared by a conventional method, through a nanofilter or the like. Specific examples thereof may include PEG-liposomes.

Herein, membrane components constituting the liposomes contain lipids as main constituents. Examples thereof may include phospholipids, glyceroglycolipids, and sphingoglycolipids.

In particular, there may be given, for example, DPPC, DSPE-PEG, DSPE-PEG-NHS, EPC, POPC, DSPC, DSPE, PS, PG, PI, DMPG, and DMPC as the phospholipids.

Examples of the particle size may include an average particle diameter of 50 to 500 nm as a size suitable for transfer in the capillaries of organs and tissues. The average particle diameter of the Bubble liposomes that may be used is preferably 50 to 200 nm, specifically 100 to 200 nm.

In this connection, the Bubble liposomes having too large a particle diameter are not suitable for transfer in the capillaries and cannot be suitably used for intravascular administration. Further, such Bubble liposomes are poor in penetration into deep tissues.

Examples of the perfluorohydrocarbon to be encapsulated into the Bubble liposomes may include perfluoromethane, perfluoroethane, perfluoropropane, perfluorobutane, perfluoropentane, perfluorohexane, perfluoroheptane, and perfluorooctane.

Specifically, perfluoropropane may be suitably used.

(Form of Drug)

The therapeutic drug for DMD of the present invention may be in any form as long as the PMO-loaded Bubble liposomes are included as an active ingredient as described above, and has only to be in a liquid form upon administration. For example, the therapeutic drug may be in a form such as a liquid ampoule or a concentrated liquid.

Further, the therapeutic drug may be mixed with a pH adjustor, an antibiotic, or the like, as necessary. Further, even the therapeutic drug in a powder, a granule, or a capsule form mixed with an excipient or the like may be used without any problem as long as it is a liquid upon use.

(Administration Method)

The therapeutic drug for DMD in the present invention needs to be administered into the body by local administration to a muscle tissue or intravascular administration. Specifically, the administration may be performed by injection, infusion, or the like.

In particular, the intravascular administration (specifically intravenous administration) is preferably performed because the active ingredient of the therapeutic drug can be delivered (spread) to muscle tissues throughout the body through the capillaries.

For the dosage of the therapeutic drug, a sufficient effect can be obtained by administering 0.1 to 500 mg, 1 to 250 mg, preferably 10 to 100 mg of the therapeutic drug in terms of the amount of the PMO in the case of an adult human having a body weight of 60 kg.

(Ultrasound Irradiation)

In the present invention, it is essential to perform the 'ultrasound irradiation' to a muscle tissue transcutaneously after the administration.

Figure 4:
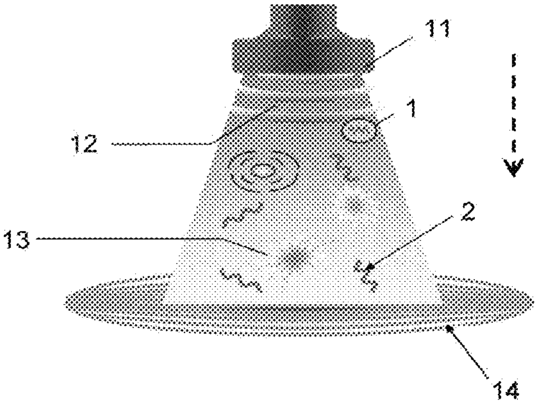
FIG. 4 is a view illustrating a mechanism in which a PMO is introduced into a muscle tissue by administration of PMO-loaded Bubble liposomes followed by application of sonication to the muscle tissue. The dotted arrow indicates an ultrasound irradiation direction.

The present invention is a technology as described below. That is, the Bubble liposomes are caused to collapse at an arbitrary site by the above-mentioned treatment, and a shock wave (cavitation) generated as a result of the collapse allows the PMO to be passed through the vascular walls (vascular endothelial cells and endomysium), and allows the PMO to be taken up (introduced) into cells of muscle fibers (muscle cells) with high efficiency. FIG. 4 illustrates a schematic view of the treatment.

In this connection, any apparatus may be used as an ultrasound irradiation apparatus as long as the ultrasound irradiation can be performed under the following irradiation conditions. For example, a dedicated ultrasound irradiation apparatus such as SONITRON or SONOPORE manufactured by NEPA GENE CO., LTD. may be used.

Further, an ultrasound diagnosis apparatus for clinical use may be utilized. In this case, the ultrasound diagnosis apparatus refers to an apparatus that irradiates a target site, on which a probe has been placed, with ultrasound transcutaneously, detects ultrasound reflection from a tissue or the like, and visualizes the inside as an image. In the present invention, the ultrasound irradiation of the present invention can be performed through the utilization of an ultrasound irradiation function of the apparatus.

Further, a high-intensity focused ultrasound apparatus (HIFU), which is used in a cancer therapy or the like, or a low-frequency ultrasound apparatus, which is used in a fracture therapy or the like, may be used in the present invention by modulating the irradiation conditions.

For conditions for the ultrasound irradiation, the ultrasound irradiation may be performed under the condition of an irradiation frequency of 0.2 to 10 MHz, preferably 0.5 to 5 MHz, more preferably 1 to 3 MHz.

Further, the ultrasound irradiation may be performed under the condition of an irradiation intensity of 0.1 to 10 $W/cm^2$, preferably 0.1 to 3 $W/cm^2$, more preferably 0.5 to 3 $W/cm^2$.

An irradiation time may be such a time as to allow the collapse of the Bubble liposomes, and may be, for example, 10 seconds or more, preferably 30 seconds or more, particularly preferably 60 seconds or more. Further, the upper limit thereof is not particularly limited, but may be, for example, 360 seconds or less, preferably 180 seconds or less, particularly preferably 120 seconds or less.

The ultrasound irradiation method can be performed by simply placing a probe of an ultrasound irradiation apparatus to a desired muscle tissue transcutaneously, and hence is an extremely safe method.

It should be noted that, when the treatment is performed for animals such as mice, an improvement in irradiation efficiency can be achieved by shaving the hair of the animals and the like prior to the treatment.

(Restoration from Symptoms of DMD)

The present invention allows high efficient PMO introduction into a wide range of muscle tissues in the vicinity of a site irradiated with ultrasound. With this, in muscle fibers (muscle cells) of a muscle tissue deficient in dystrophin, the expression of the protein can be dramatically restored.

For example, when intravenous injection is performed under compressing the upper hind limbs with a tourniquet and the hind limbs are irradiated with ultrasound, the entirety ('wide range') of skeletal muscles of the hind limbs can be treated.

Further, in the present invention, the symptoms of DMD can also be dramatically ameliorated by performing intravascular administration 'at least once.'

In addition, in the present invention, when 'arbitrary' muscle tissues of the whole body are irradiated with ultrasound after systemic administration via blood vessels, the treatment of the arbitrary muscle tissues of the whole body ('systemic therapy') can be realized.

In particular, also in the muscle tissues of the 'heart and diaphragm' (muscle tissues that cause heart failure and respiratory distress along with the progression of DMD, respectively), into which the PMO has been almost unable to be introduced by a conventional method, the therapy for DMD can be performed by irradiating these sites with ultrasound.

EXAMPLES

Hereinafter, the present invention is described by way of Examples. However, the scope of the present invention is by no means limited by Examples shown below.

Preparation Example 1

Preparation of PMO-loaded Bubble Liposomes (1) Preparation of Liposomes

Two kinds of basic lipids, i.e., dipalmitoylphosphatidylcholine (DPPC: manufactured by NOF Corporation) and distearoylphosphatidylethanolamine-$PEG_{2000}$-OMe (DSPE-$PEG_{2000}$-OMe: manufactured by NOF Corporation) were used and dissolved in a solution of chloroform:diisopropyl ether:PBS=1:1:1 so that the lipid composition was DPPC: DSPE-$PEG_{2000}$-OMe=94:6 (molar ratio).

The solution was sonicated with a probe-type sonicator (20 kHz) and then the organic solvent was removed with a rotary evaporator to yield liposomes (PEG-liposomes).

The resultant liposomes were freeze-thawed and then passed through a poly carbonate membrane having a pore size of 0.2 μm using Extruder (Lipex Biomembrane Inc.) so that the particle diameter was adjusted to about 100 to 200 nm. After that, the resultant liposomes were subjected to filter sterilization with a cellulose acetate syringe filter having a pore size of 0.45 μm and then used for experiments.

(2) Preparation of Bubble Liposomes 2 mL of the prepared liposomes (lipid concentration: 1 mg/mL) were charged into a 5-mL vial filled with perfluoropropane.

Sonicating with a bath-type sonicator (42 kHz), a suspension of Bubble liposomes encapsulating perfluoropropan was prepared.

(3) Preparation of PMO-loaded Bubble Liposomes

A PMO having a base sequence set forth in SEQ ID NO: 4 (PMO for exon 23 in the dystrophin gene of an mdx mouse, GENE TOOLS, LLC, concentration: 10 μg/10 μL) dissolved in sterile water was added to the Bubble liposomes (total lipid amount: 30 μg/30 μL), followed by small oscillation for a predetermined time, to thereby prepare PMO-loaded Bubble liposomes. FIG. 1 illustrates a schematic view of each of the PMO-loaded Bubble liposomes.

It should be noted that it is estimated that the PMO is not encapsulated into the Bubble liposomes but is loaded in a state of being fitted in (in a state of being bound to) the grooves of surfaces thereof.

Test Example 1

Study on PMO Loading Capacity

To the Bubble liposomes (total lipid amount: 60 μg/60 μL) was added an FITC-labeled PMO so that the addition amounts were 0, 25, 50, 100, 150, and 200 pmol to prepare PMO-loaded Bubble liposomes having different addition amounts. It should be noted that the other preparation procedures were performed in the same manner as in the method described in Preparation Example 1.

Figure 5:
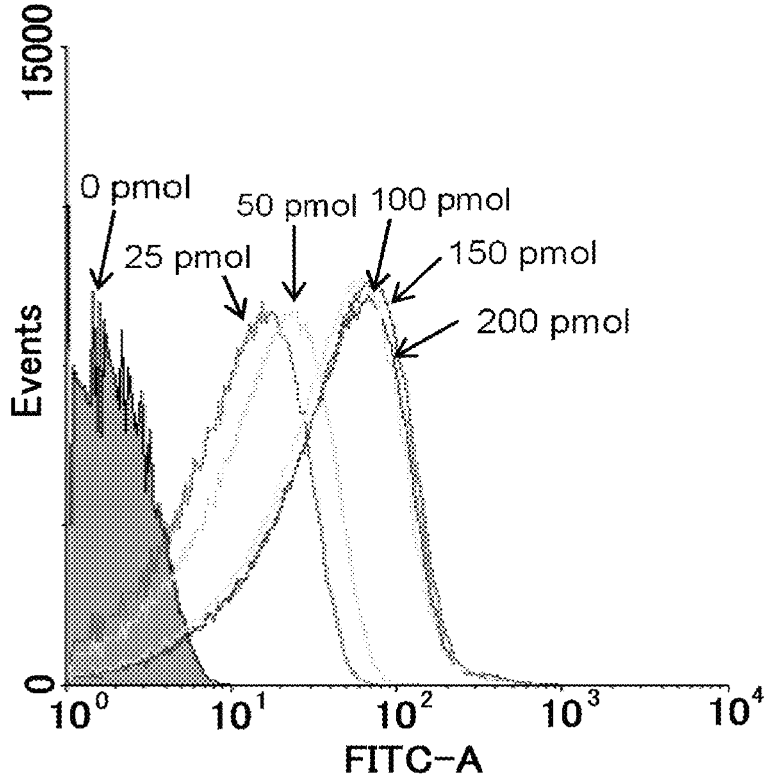
FIG. 5 shows the results of measurement of the PMO loading capacity of Bubble liposomes by FACS analysis in Test Example 1.

Then, the PMO loading capacity of each of the prepared Bubble liposomes was measured by fluorescence activated cell sorting (FACS) analysis. FIG. 5 shows the results.

The results showed that the PMO can be loaded depending on the addition amount until the addition amount of the PMO became 100 pmol with respect to the Bubble liposomes having a total lipid amount of 60 μg/60 μL (i.e., the addition amount of the PMO became 1.67 μmol with respect to the Bubble liposomes having a total lipid amount of 1 mg/ml).

Example 1

Introduction of PMO by Intramuscular Administration to Tibialis (1) Introduction of PMO The solution of the PMO-loaded Bubble liposomes (PMO amount: 10 μg) prepared in Preparation Example 1 was intramuscularly administered (locally administered) to the tibialis of 5 to 6-week-old mdx mice (dystrophy protein-deficient mice).

Immediately after that, a probe of an ultrasound irradiation apparatus (SONITRON 2000, NEPA GENE, CO, LTD.) was placed to the tibialis (hind limb), and ultrasound irradiation (frequency: 1 MHz, duty: 50%, intensity: 2 $W/cm^2$, time: 60 sec.) was performed transcutaneously.

Then after the ultrasound irradiation, the mice were bred by a conventional method for 2 weeks. Further, as a comparative control, the mdx mice were treated by administering the same amount of only the PMO, and bred in the same manner. Further, as a control, normal mdx mice were bred in the same manner.

(2) Detection of Exon Skipping-induced mRNA by Nested RT-PCR Method

Figure 6:
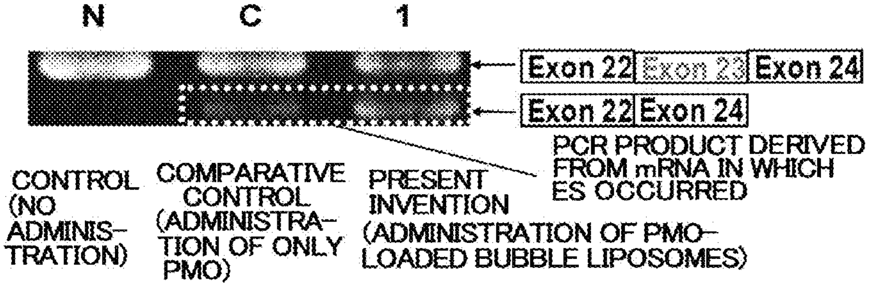
FIG. 6 is an electropherogram showing the detection of the presence or absence of exon skipping induction by RT-PCR in Example 1.

After a lapse of 2 weeks from the PMO introduction treatment, the efficiency of skipping exon 23 (having a stop codon resulting from a mutation in the mdx mice) of dystrophin mRNA by the PMO introduction was analyzed by the method of Analysis Example 1. FIG. 6 shows the results. (It should be noted that the exon skipping is hereinafter sometimes simply abbreviated as "ES.")

The results showed that a band appearing upon the occurrence of the exon skipping in the dystrophin gene was not detected in a normal mdx mouse (control: lane N of FIG. 6), whereas the exon skipping in the dystrophin gene was remarkably induced in the group that received the PMO-loaded Bubble liposomes (present invention: lane 1 of FIG. 6).

The results also showed that the intensity of the band was significantly increased as compared to the case where only the PMO was administered (comparative control: lane C of FIG. 6).

(3) Detection of Dystrophin Expression by Immunostaining Method

Figure 7:
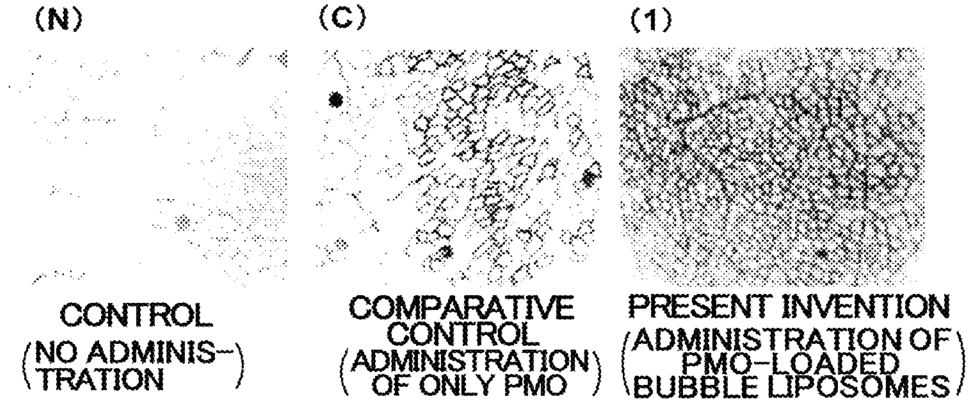
FIG. 7 are photographic images each showing the detection of the expression of a dystrophin protein by immunostaining in Example 1.
Figure 8:
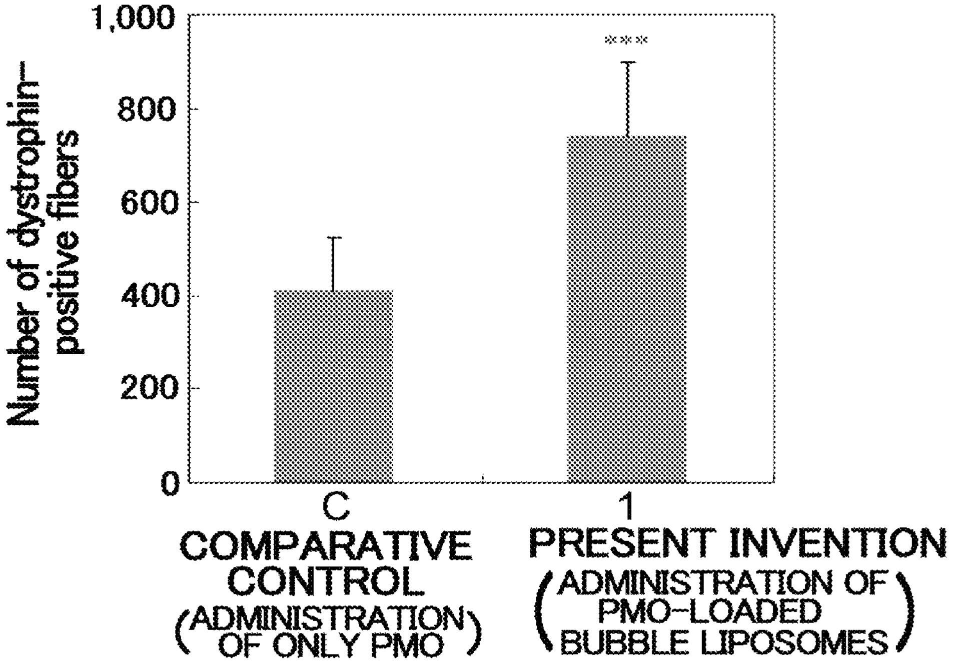
FIG. 8 is a graph showing the counting of the number of cells expressing the dystrophin protein detected by immunostaining in Example 1.

Further, after a lapse of 2 weeks from the PMO introduction treatment, dystrophin expression induced in the muscle tissues of the mdx mice by the PMO introduction was detected by the method of Analysis Example 2. FIGS. 7 and 8 show the results.

The results showed that the dystrophin protein was not expressed in the normal mdx mouse (control: FIG. 7(N)), whereas the expression of the dystrophin protein was remarkably restored in the group that received the PMO-loaded Bubble liposomes (present invention: FIG. 7(1)).

The results also showed that the number of muscle fibers expressing the dystrophin protein was significantly increased as compared to the case where only the PMO was administered (comparative control: FIG. 7(C)) (FIG. 8).

Example 2

Introduction of PMO by Transvenous Administration to Hind-limb Muscle Tissues (1) Introduction of PMO While the upper hind limbs of 5 to 6-week-old mdx mice were compressed with a tourniquet, the solution of the PMO-loaded Bubble liposomes (PMO amount: 50 μg) prepared in Preparation Example 1 was administered from the great saphenous vein (transvenous administration) with a syringe pump (KDS100, kdScientific) at a constant flow rate.

Figure 9:
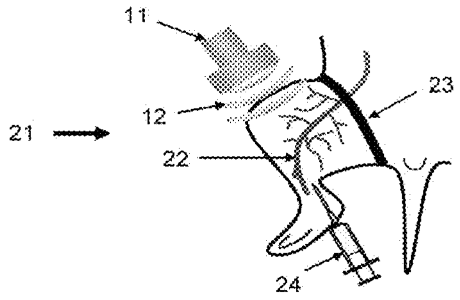
FIG. 9 is a view illustrating the outline of experimental operations in Example 2.

Immediately after that, a probe of an ultrasound irradiation apparatus (SONITRON 2000, NEPA GENE, CO, LTD.) was attached to the hind-limb skeletal muscles (hind limb), and ultrasound irradiation (frequency: 1 MHz, duty: 50%, intensity: 2 W/$cm^2$, time: 120 sec.) was performed transcutaneously. FIG. 9 illustrates a schematic view of the operation.

Then after the ultrasound irradiation, the mice were bred by a conventional method for 2 weeks. Further, as a comparative control, the mdx mice were treated by administering the same amount of only the PMO, and bred in the same manner. Further, as a control, normal mdx mice were bred in the same manner.

It should be noted that Table 1 shows the kinds of hind-limb skeletal muscles analyzed below. Further, FIG. 10 illustrate schematic views of the skeletal muscles.

TABLE 1

Figure 10:
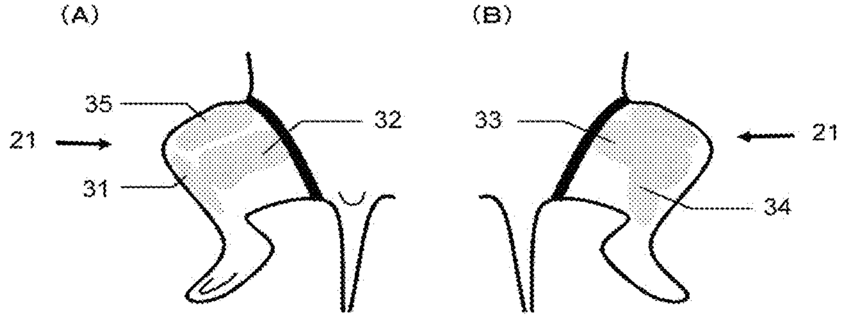
FIG. 10 are views schematically illustrating mouse hindlimb skeletal muscles.
Figure 11:
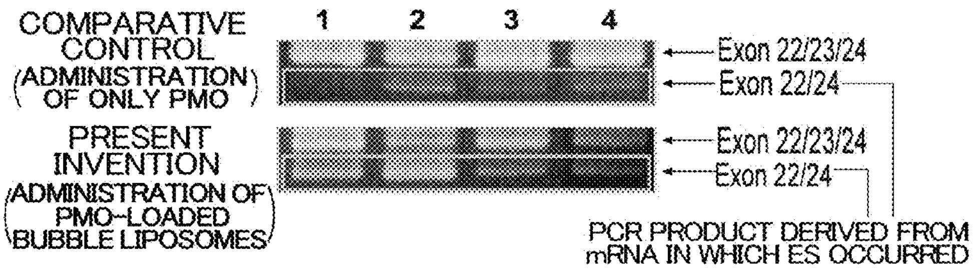
FIG. 11 are electropherograms each showing the detection of the presence or absence of exon skipping induction by RT-PCR in Example 2.
Figure 12:
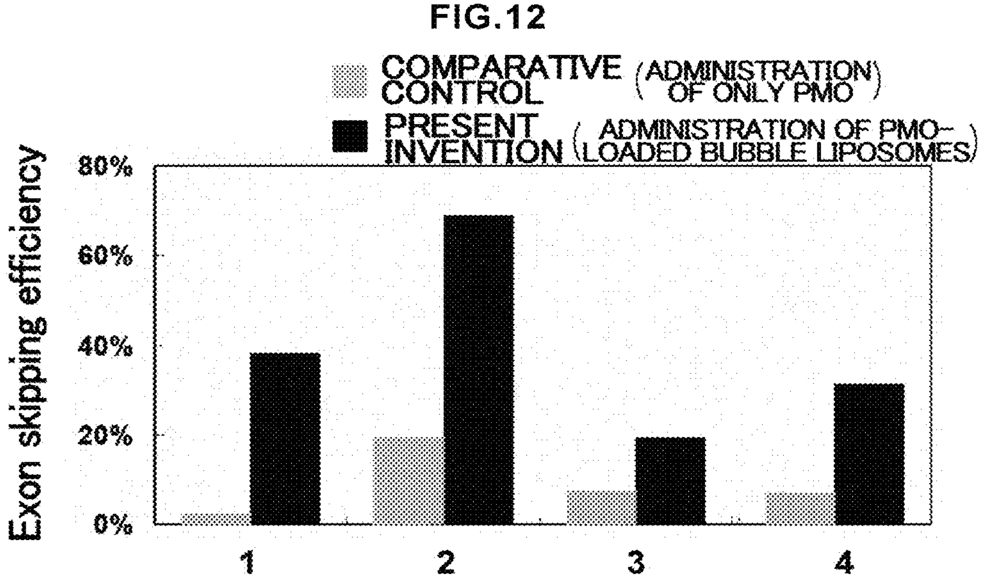
FIG. 12 is a graph showing exon skipping induction efficiencies calculated from the results of RT-PCR in Example 2.
Figure 13:
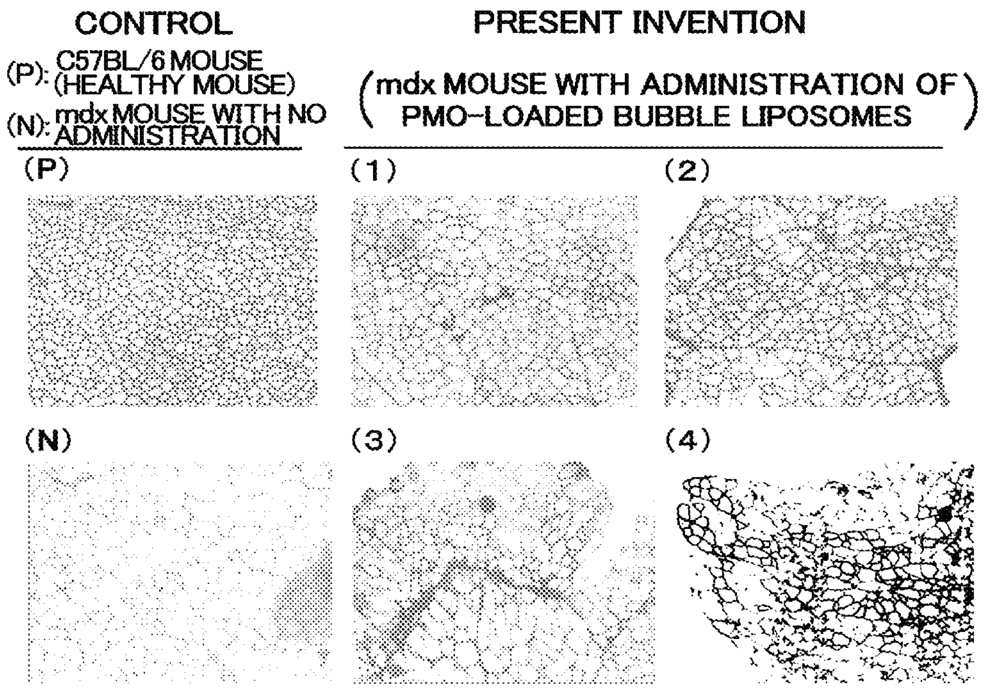
FIG. 13 are photographic images each showing the detection of the expression of the dystrophin protein by immunostaining in Example 2.

| | Reference numerals in FIGS. 10 | Reference numerals in FIGS. 11 to 13 |
|---|---|---|
| Tibialis | 31 | 1 |
| Hamstring | 32 | 2 |
| Biceps | 33 | 3 |
| Gastrocnemius | 34 | 4 |

(2) Detection of Exon Skipping-induced mRNA by Nested RT-PCR Method

After a lapse of 2 weeks from the PMO introduction treatment, the efficiency of skipping exon 23 of dystrophin mRNA by the PMO introduction was analyzed by the method of Analysis Example 1. FIGS. 11 and 12 show the results.

The results showed that the exon skipping in the dystrophin gene was remarkably induced throughout a wide range of the hind-limb skeletal muscles in the group that received the PMO-loaded Bubble liposomes (present invention) as compared to the group that received only the PMO (comparative control).

(3) Detection of Dystrophin Expression by Immunostaining Method

Further, after a lapse of 2 weeks from the PMO introduction treatment, dystrophin expression induced in the muscle tissues of the mdx mice by the PMO introduction was detected by the method of Analysis Example 2. FIG. 13 show the results. It should be noted that the hind-limb skeletal muscle tissue of a healthy C57BL/6 mouse that did not develop muscular dystrophin was used as a positive control (healthy mouse: FIG. 13(P)).

The results showed that the dystrophin protein was not expressed in the hind-limb skeletal muscle of the normal mdx mouse (control: FIG. 13(N)), whereas the expression of the dystrophin protein was remarkably restored throughout a wide range of the hind-limb skeletal muscles in the group that received the PMO-loaded Bubble liposomes (present invention: FIGS. 13(1) to 13(4)).

Example 3

Introduction of PMO into Heart (1) Introduction of PM

200 μl of the solution of the PM-loaded Bubble liposomes (PMO amount: 500 μg) prepared in Preparation Example 1 was administered to the tail veins of 5 to 6-week-old mdx mice.

Figure 14:
FIG. 14 is a photographic image obtained by photographing the situation of sonication in Example 3.

Immediately after that, a probe of an ultrasound irradiation apparatus (SONITRON 2000, NEPA GENE, CO, LTD.) was placed to the heart (chest), and ultrasound irradiation (frequency: 1 MHz, duty: 50%, intensity: 2 W/$cm^2$, time: 60 sec.) was performed transcutaneously. FIG. 14 shows a photographic image obtained by photographing the situation of the treatment.

(2) Detection of Dystrophin Expression by Immunostaining Method

Figure 15:
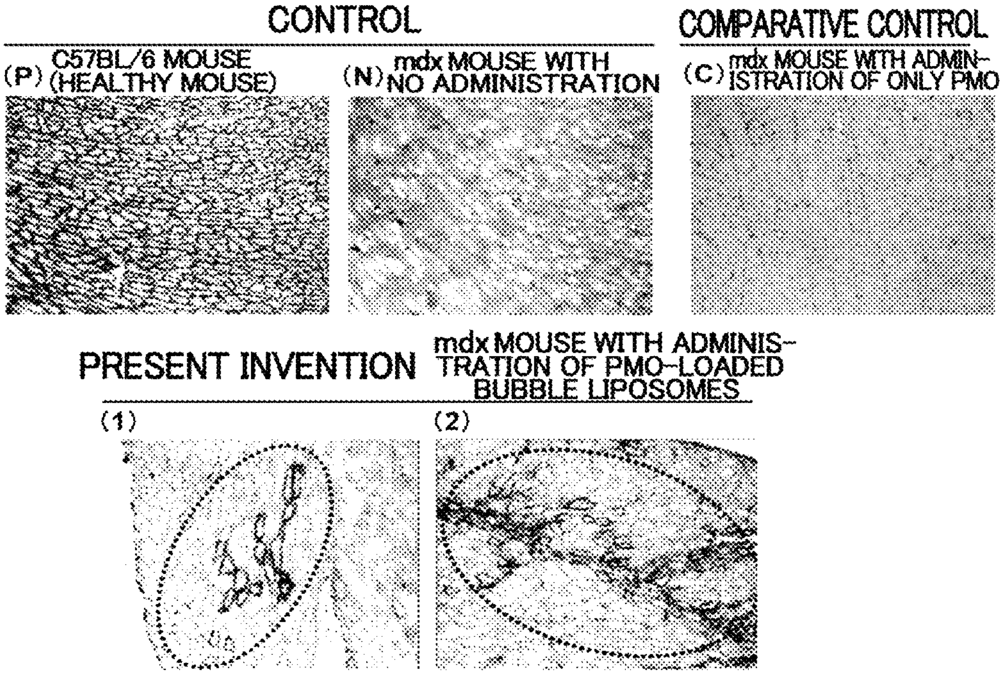
FIG. 15 are photographic images each showing the detection of the expression of the dystrophin protein by immunostaining in Example 3.

After a lapse of 2 weeks from the PMO introduction treatment, dystrophin expression induced in the muscle tissues of the mdx mice by the PMO introduction was detected by the method of Analysis Example 2. FIG. 15 show the results. It should be noted that the cardiac muscle tissue of a healthy C57BL/6 mouse that did not develop muscular dystrophin was used as a positive control (healthy mouse: FIG. 15(P)).

The results showed that the dystrophin protein was not expressed in the cardiac muscle tissues of a normal mdx mouse (control: FIG. 15(N)) and the group that received only the PMO (comparative control: FIG. 15(C)), whereas the expression of the dystrophin protein was restored in the group that received the PMO-loaded Bubble liposomes (present invention: FIGS. 15(1) and 15(2)).

(Discussion on Examples 1 to 3)

i) It was revealed that the dystrophin expression was able to be significantly restored by administering the PMO-loaded Bubble liposomes and sonicating a target site, as compared to the conventional case where only the PMO was administered.

It should be noted that it was confirmed that the restoration of the dystrophin expression was attributed to the synthesis of mRNA in which exon 23 was skipped by the action of the PMO.

ii) It was suggested that the dystrophin expression was able to be restored in 'arbitrary' and a 'wide range' of muscle tissues by intravenously injecting the PMO-loaded Bubble liposomes (systemic administration) and irradiating arbitrary sites with ultrasound.

iii) Further, it was shown that a dramatic restoration effect was obtained by performing the administration 'only once,' although it had been essential to perform the administration frequently in the past.

iv) It was shown that the dystrophin expression was able to be restored also in the 'heart (cardiac muscle),' into which it had been difficult to introduce the PMO in the past.

Analysis Example 1

Detection of Exon Skipping-induced mRNA by Nested RT-PCR Method

An exon skipping induction efficiency by PMO introduction was analyzed by performing nested RT-PCR using two primer sets designed on exon 20 and exon 26 of a mouse dystrophin gene.

Extraction of Total RNA

Muscle tissues were collected from the mice and homogenized with addition of RNAiso Plus (TaKaRa). After that, the homogenate was centrifuged at 12,000 g and 4° C. for 5 minutes and then the supernatant was collected.

Chloroform was added and mixed into the supernatant, and the mixture was left to stand at room temperature for 5 minutes and then centrifuged at 12,000 g and 4° C. for 15 minutes. The aqueous layer as the upper layer was collected.

Isopropanol was added to the aqueous layer, and the mixture was centrifuged at 12,000 g and 4° C. for 10 minutes, washed with addition of 75% ethanol, and centrifuged at 7,500 g and 4° C. for 5 minutes. After that, the supernatant was discarded and the pellet was dried.

The resultant precipitate was dissolved in DEPC-treated water to prepare a total RNA solution. The concentration of RNA was calculated by measuring an absorbance at 260 nm.

cDNA Synthesis (Reverse Transcription)

To total RNA (1 μg) were added 1 μL of Oligo dT (Invitrogen), 1 μL of dNTP mix (Invitrogen), and DEPC-treated water so that the total volume was 10 μL. Then, the resultant was subjected to thermal denaturation by treatment at 65° C. for 5 minutes and immediately cooled with ice to inhibit the formation of higher-order structures of RNA molecules.

To the above-mentioned liquid were added 4 μL of 5× Prime Script (TaKaRa), 0.5 μL of RNase Out inhibitor (Invitrogen), 0.5 μL of Prime Script (RTase, TaKaRa), and 5 μL of DEPC-treated water so that the total volume was 20 μL. Then, an elongation reaction was performed at 42° C. for 60 minutes, and RTase was inactivated at 70° C. for 15 minutes to stop the reaction. Thus, a cDNA solution was prepared.

Nested PCR

To 2 μL of the cDNA solution were added 1 μL of a 10 μM forward primer (Exon20Fo: primer designed on exon 20 and set forth in SEQ ID NO: 5), 1 μL of a 10 μM reverse primer (Exon26Ro: primer designed on exon 26 and set forth in SEQ ID NO: 6), 0.125 μL of Ex Taq (TaKaRa), 2.5 μL of 10×Ex Taq buffer, 2.0 μL of 10 mM dNTP Mixture, and 16.375 μL of sterile distilled water so that the total volume was 25 μL.

Then, 30 cycles of the following steps were performed: thermal denaturation at 95° C. for 30 seconds; annealing at 55° C. for 1 minute; and an elongation reaction at 72° C. for 2 minutes.

Subsequently, to 1 μL of the resultant 1st PCR product were added 1 μL of a 10 μM forward primer (Exon20Fi: primer designed on exon 20 and set forth in SEQ ID NO: 7), 1 μL of a 10 μM reverse primer (Exon26Ri: primer designed on exon 26 and set forth in SEQ ID NO: 8), 0.125 μL of Ex Taq, 2.5 μL of 10×Ex Taq buffer, 2.0 μL of 10 mM dNTP Mixture, and 17.375 μL of sterile distilled water. Then, 25 cycles of the following steps were performed: thermal denaturation at 95° C. for 1 minute; annealing at 57° C. for 1 minute; and an elongation reaction at 72° C. for 2 minutes.

To the resultant 2nd PCR product was added a 6× loading buffer, and the mixture was subjected to electrophoresis under a constant voltage of 100 V for about 50 minutes through the use of a 2% agarose gel prepared with a TBE solution. After the electrophoresis, the gel was immersed in a TBE solution containing SYBR safe (Invitrogen) and stained at room temperature for about 30 minutes. The band of DNA was detected by UV irradiation (Epi-Light UV FA 1100).

Calculation of Exon Skipping Induction Efficiency

The band intensity of the PCR product detected in the foregoing was analyzed with ImageJ software. Then, the exon skipping (ES) induction efficiency was calculated from the resultant numerical value for the band intensity according to the following equation (1).

[Math. 1]

$$\text{ES induction efficiency}=\text{Value for band intensity with ES}/(\text{Value for band intensity with ES}+\text{Value for band intensity without ES}) \quad (1)$$

Analysis Example 2

Detection of Dystrophin Expression by Immunostaining Method

The dystrophin expression induced in the muscle tissues of the mdx mice by the PMO introduction was detected by performing immunostaining using an antibody against the dystrophin protein.

The PMO-introduced tissues were collected from the mice, embedded in O.C.T. Compound (Sakura Finetek Japan), frozen on dry ice, and then preserved at −80° C.

After that, sections were prepared from the frozen tissues with a cryostat. The sections were washed with TBST and then subjected to a reaction with a primary antibody NCL-DYS2 (Novocastra) at room temperature for 1 hour. The resultant sections were washed with TBST and then subjected to a reaction with a secondary antibody Alexa Fluor 546 (MolecularProbes) at room temperature for 1 hour.

The resultant sections were washed with TBST, then mounted with VECTASHIELD Hard•Set Mounting Medium with DAPI (Funakoshi Corporation), and observed with a fluorescent microscope (Axiovert 200M: Carl Zeiss, KEYENCE: BZ8100) to detect the expression of the dystrophin protein.

INDUSTRIAL APPLICABILITY

The therapeutic drug for DMD of the present invention can dramatically ameliorate symptoms of a severe DMD patient for whom there is no effective therapeutic method under the present circumstances. Further, the therapeutic drug for DMD of the present invention can significantly reduce administration burdens to improve the QOL of DMD patients.

With this, the present invention is expected to be able to make contributions in the fields of medicine and pharmacy.

REFERENCE SIGNS LIST

1: PMO-loaded Bubble liposome
2: PMO
3: PEG
4: perfluorohydrocarbon
5: lipid bilayer membrane
11: probe for ultrasound irradiation
12: ultrasound
13: jet flow with cavitation
14: muscle tissue
21: mouse hind limb
22: great saphenous vein
23: tourniquet
24: syringe pump
31: tibialis
32: hamstring
33: biceps
34: gastrocnemius
35: quadriceps

The invention claimed is:

1. A method for treating Duchenne muscular dystrophy in a subject in need thereof, the method comprising:

administering a Bubble liposome and a morpholino oligomer bound to a surface of the Bubble liposome into a blood vessel of the subject, and transcutaneously irradiating a muscle tissue with ultrasound, wherein the morpholino oligomer in a splicing process for a pre-mRNA of a dystrophin gene having a stop codon resulting from a mutation, produces a mature mRNA skipping an exon having the mutation therein;

the morpholino oligomer comprises a base sequence complementary to a region comprising a splicing enhancer sequence for said exon having the mutation therein; and the morpholino oligomer has a polymerization degree of from 15 to 50 mer.

2. The method according to claim 1, wherein said exon having the mutation therein comprises any one of exons 2, 8, 23, 43 to 46, and 50 to 53.

3. The method according to claim 1, wherein the Bubble liposome comprises a PEG-liposome encapsulating a perfluorohydrocarbon, and the Bubble liposome has an average particle diameter of from 50 to 500 nm.

4. The method according to claim 1, wherein the administering comprises systemic administration via the great saphenous vein.

5. The method according to claim 4, wherein the muscle tissue comprises a heart muscle tissue, a diaphragm muscle tissue, or both.

* * * * *

SEQUENCE LISTING

```
<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: PMO to act as inducing exon skipping for human
      dystrophin(DMD) exon 46

<400> SEQUENCE: 1

gcttttcttt tagttgctgc tc                                            22


<210> SEQ ID NO 2
<211> LENGTH: 29
<212> TYPE: DNA
<213> ORGANISM: Artificial Sequence
<220> FEATURE:
<223> OTHER INFORMATION: PMO to act as inducing exon skipping for human
      dystrophin(DMD) exon 50

<400> SEQUENCE: 2

ccactcagag ctcagatctt ctaacttcc                                     29


<210> SEQ ID NO 3
<211> LENGTH: 30
<212> TYPE: DNA
<213> ORGANISM: Artificial Sequence
<220> FEATURE:
<223> OTHER INFORMATION: PMO to act as inducing exon skipping for human
      dystrophin(DMD) exon 51

<400> SEQUENCE: 3

ctccaacatc aaggaagatg gcatttctag                                    30


<210> SEQ ID NO 4
<211> LENGTH: 25
<212> TYPE: DNA
<213> ORGANISM: Artificial Sequence
<220> FEATURE:
<223> OTHER INFORMATION: PMO to act as inducing exon skipping for
      mdx-mouse dystrophin(DMD) exon 23

<400> SEQUENCE: 4

ggccaaacct cggcttacct gaaat                                         25


<210> SEQ ID NO 5
<211> LENGTH: 22
<212> TYPE: DNA
<213> ORGANISM: Artificial Sequence
<220> FEATURE:
<223> OTHER INFORMATION: PCR primer: Exon20Fo

<400> SEQUENCE: 5

cagaattctg ccaattgctg ag                                            22


<210> SEQ ID NO 6
<211> LENGTH: 20
<212> TYPE: DNA
<213> ORGANISM: Artificial Sequence
<220> FEATURE:
<223> OTHER INFORMATION: PCR primer: Exon26Ro

<400> SEQUENCE: 6

ttcttcagct tgtgtcatcc                                               20
```

-continued

<210> SEQ ID NO 7
<211> LENGTH: 24
<212> TYPE: DNA
<213> ORGANISM: Artificial Sequence
<220> FEATURE:
<223> OTHER INFORMATION: PCR primer: Exon20Fi

<400> SEQUENCE: 7
cccagtctac caccctatca gagc 24

<210> SEQ ID NO 8
<211> LENGTH: 19
<212> TYPE: DNA
<213> ORGANISM: Artificial Sequence
<220> FEATURE:
<223> OTHER INFORMATION: PCR primer: Exon26Ri

<400> SEQUENCE: 8
cctgccttta agcttcctt 19

<210> SEQ ID NO 9
<211> LENGTH: 11058
<212> TYPE: DNA
<213> ORGANISM: Homo sapiens
<220> FEATURE:
<221> NAME/KEY: misc_feature
<222> LOCATION: (1)..(11058)
<223> OTHER INFORMATION: Human dystrophin gene CDS

<400> SEQUENCE: 9
atgctttggt gggaagaagt agaggactgt tatgaaagag aagatgttca aaagaaaaca 60
ttcacaaaat gggtaaatgc acaattttct aagtttggga agcagcatat tgagaacctc 120
ttcagtgacc tacaggatgg gaggcgcctc ctagacctcc tcgaaggcct gacagggcaa 180
aaactgccaa aagaaaaagg atccacaaga gttcatgccc tgaacaatgt caacaaggca 240
ctgcgggttt tgcagaacaa taatgttgat ttagtgaata ttggaagtac tgacatcgta 300
gatggaaatc ataaactgac tcttggtttg atttggaata taatcctcca ctggcaggtc 360
aaaaatgtaa tgaaaaatat catggctgga ttgcaacaaa ccaacagtga aaagattctc 420
ctgagctggg tccgacaatc aactcgtaat tatccacagg ttaatgtaat caacttcacc 480
accagctggt ctgatggcct ggctttgaat gctctcatcc atagtcatag gccagaccta 540
tttgactgga atagtgtggt ttgccagcag tcagccacac aacgactgga acatgcattc 600
aacatcgcca gatatcaatt aggcatagag aaactactcg atcctgaaga tgttgatacc 660
acctatccag ataagaagtc catcttaatg tacatcacat cactcttcca agttttgcct 720
caacaagtga gcattgaagc catccaggaa gtggaaatgt tgccaaggcc acctaaagtg 780
actaaagaag aacattttca gttacatcat caaatgcact attctcaaca gatcacggtc 840
agtctagcac agggatatga gagaacttct tcccctaagc ctcgattcaa gagctatgcc 900
tacacacagg ctgcttatgt caccacctct gaccctacac ggagcccatt tccttcacag 960
catttggaag ctcctgaaga caagtcattt ggcagttcat tgatggagag tgaagtaaac 1020
ctggaccgtt atcaaacagc tttagaagaa gtattatcgt ggcttctttc tgctgaggac 1080
acattgcaag cacaaggaga gatttctaat gatgtggaag tggtgaaaga ccagtttcat 1140
actcatgagg ggtacatgat ggatttgaca gcccatcagg gccgggttgg taatattcta 1200
caattgggaa gtaagctgat tggaacagga aaattatcag aagatgaaga aactgaagta 1260
caagagcaga tgaatctcct aaattcaaga tgggaatgcc tcagggtagc tagcatggaa 1320

-continued

```
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac agatttcaca ggctgtcacc accactcagc catcactaac acagacaact   2040
gtaatggaaa cagtaactac ggtgaccaca agggaacaga tcctggtaaa gcatgctcaa   2100
gaggaacttc caccaccacc tccccaaaag aagaggcaga ttactgtgga ttctgaaatt   2160
aggaaaaggt tggatgttga tataactgaa cttcacagct ggattactcg ctcagaagct   2220
gtgttgcaga gtcctgaatt tgcaatcttt cggaaggaag gcaacttctc agacttaaaa   2280
gaaaaagtca atgccataga gcgagaaaaa gctgagaagt tcagaaaact gcaagatgcc   2340
agcagatcag ctcaggccct ggtggaacag atggtgaatg agggtgttaa tgcagatagc   2400
atcaaacaag cctcagaaca actgaacagc cggtggatcg aattctgcca gttgctaagt   2460
gagagactta actggctgga gtatcagaac aacatcatcg ctttctataa tcagctacaa   2520
caattggagc agatgacaac tactgctgaa aactggttga aaatccaacc caccacccca   2580
tcagagccaa cagcaattaa aagtcagtta aaaatttgta aggatgaagt caaccggcta   2640
tcaggtcttc aacctcaaat tgaacgatta aaaattcaaa gcatagccct gaaagagaaa   2700
ggacaaggac ccatgttcct ggatgcagac tttgtggcct ttacaaatca ttttaagcaa   2760
gtcttttctg atgtgcaggc cagagagaaa gagctacaga caatttttga cactttgcca   2820
ccaatgcgct atcaggagac catgagtgcc atcaggacat gggtccagca gtcagaaacc   2880
aaactctcca tacctcaact tagtgtcacc gactatgaaa tcatggagca gagactcggg   2940
gaattgcagg ctttacaaag ttctctgcaa gagcaacaaa gtggcctata ctatctcagc   3000
accactgtga aagagatgtc gaagaaagcg ccctctgaaa ttagccggaa atatcaatca   3060
gaatttgaag aaattgaggg acgctggaag aagctctcct cccagctggt tgagcattgt   3120
caaaagctag aggagcaaat gaataaactc cgaaaaattc agaatcacat acaaaccctg   3180
aagaaatgga tggctgaagt tgatgttttt ctgaaggagg aatggcctgc ccttggggat   3240
tcagaaattc taaaaaagca gctgaaacag tgcagacttt tagtcagtga tattcagaca   3300
attcagccca gtctaaacag tgtcaatgaa ggtgggcaga agataaagaa tgaagcagag   3360
ccagagtttg cttcgagact tgagacagaa ctcaaagaac ttaacactca gtgggatcac   3420
atgtgccaac aggtctatgc cagaaaggag gccttgaagg gaggtttgga gaaaactgta   3480
agcctccaga aagatctatc agagatgcac gaatggatga cacaagctga agaagagtat   3540
cttgagagag attttgaata taaaactcca gatgaattac agaaagcagt tgaagagatg   3600
aagagagcta aagaagaggc ccaacaaaaa gaagcgaaag tgaaactcct tactgagtct   3660
gtaaatagtg tcatagctca agctccacct gtagcacaag aggccttaaa aaaggaactt   3720
```

-continued gaaactctaa ccaccaacta ccagtggctc tgcactaggc tgaatgggaa atgcaagact 3780
ttggaagaag tttgggcatg ttggcatgag ttattgtcat acttggagaa agcaaacaag 3840
tggctaaatg aagtagaatt taaacttaaa accactgaaa acattcctgg cggagctgag 3900
gaaatctctg aggtgctaga ttcacttgaa aatttgatgc gacattcaga ggataaccca 3960
aatcagattc gcatattggc acagacccta acagatggcg gagtcatgga tgagctaatc 4020
aatgaggaac ttgagacatt taattctcgt tggagggaac tacatgaaga ggctgtaagg 4080
aggcaaaagt tgcttgaaca gagcatccag tctgcccagg agactgaaaa atccttacac 4140
ttaatccagg agtccctcac attcattgac aagcagttgg cagcttatat tgcagacaag 4200
gtggacgcag ctcaaatgcc tcaggaagcc cagaaaatcc aatctgattt gacaagtcat 4260
gagatcagtt tagaagaaat gaagaaacat aatcagggga aggaggctgc ccaaagagtc 4320
ctgtctcaga ttgatgttgc acagaaaaaa ttacaagatg tctccatgaa gtttcgatta 4380
ttccagaaac cagccaattt tgagctgcgt ctacaagaaa gtaagatgat tttagatgaa 4440
gtgaagatgc acttgcctgc attggaaaca aagagtgtgg aacaggaagt agtacagtca 4500
cagctaaatc attgtgtgaa cttgtataaa agtctgagtg aagtgaagtc tgaagtggaa 4560
atggtgataa agactggacg tcagattgta cagaaaaagc agacggaaaa tcccaaagaa 4620
cttgatgaaa gagtaacagc tttgaaattg cattataatg agctgggagc aaaggtaaca 4680
gaaagaaagc aacagttgga gaaatgcttg aaattgtccc gtaagatgcg aaaggaaatg 4740
aatgtcttga cagaatggct ggcagctaca gatatggaat tgacaaagag atcagcagtt 4800
gaaggaatgc ctagtaattt ggattctgaa gttgcctggg gaaaggctac tcaaaaagag 4860
attgagaaac agaaggtgca cctgaagagt atcacagagg taggagaggc cttgaaaaca 4920
gttttgggca agaaggagac gttggtggaa gataaactca gtcttctgaa tagtaactgg 4980
atagctgtca cctcccgagc agaagagtgg ttaaatcttt tgttggaata ccagaaacac 5040
atggaaactt ttgaccagaa tgtggaccac atcacaaagt ggatcattca ggctgacaca 5100
cttttggatg aatcagagaa aaagaaaccc cagcaaaaag aagacgtgct taagcgttta 5160
aaggcagaac tgaatgacat acgcccaaag gtggactcta cacgtgacca agcagcaaac 5220
ttgatggcaa accgcggtga ccactgcagg aaattagtag agccccaaat ctcagagctc 5280
aaccatcgat ttgcagccat ttcacacaga attaagactg gaaaggcctc cattcctttg 5340
aaggaattgg agcagtttaa ctcagatata caaaaattgc ttgaaccact ggaggctgaa 5400
attcagcagg gggtgaatct gaaagaggaa gacttcaata aagatatgaa tgaagacaat 5460
gagggtactg taaaagaatt gttgcaaaga ggagacaact tacaacaaag aatcacagat 5520
gagagaaaga gagaggaaat aaagataaaa cagcagctgt tacagacaaa acataatgct 5580
ctcaaggatt tgaggtctca aagaagaaaa aaggctctag aaatttctca tcagtggtat 5640
cagtacaaga ggcaggctga tgatctcctg aaatgcttgg atgacattga aaaaaaatta 5700
gccagcctac ctgagcccag agatgaaagg aaaataaagg aaattgatcg ggaattgcag 5760
aagaagaaag aggagctgaa tgcagtgcgt aggcaagctg agggcttgtc tgaggatggg 5820
gccgcaatgg cagtggagcc aactcagatc cagctcagca agcgctggcg ggaaattgag 5880
agcaaatttg ctcagtttcg aagactcaac tttgcacaaa ttcacactgt ccgtgaagaa 5940
acgatgatgg tgatgactga agacatgcct ttggaaattt cttatgtgcc ttctacttat 6000
ttgactgaaa tcactcatgt ctcacaagcc ctattagaag tggaacaact tctcaatgct 6060

-continued

```
cctgacctct gtgctaagga ctttgaagat ctctttaagc aagaggagtc tctgaagaat   6120
ataaaagata gtctacaaca aagctcaggt cggattgaca ttattcatag caagaagaca   6180
gcagcattgc aaagtgcaac gcctgtggaa agggtgaagc tacaggaagc tctctcccag   6240
cttgatttcc aatgggaaaa agttaacaaa atgtacaagg accgacaagg gcgatttgac   6300
agatctgttg agaaatggcg gcgttttcat tatgatataa agatatttaa tcagtggcta   6360
acagaagctg aacagtttct cagaaagaca caaattcctg agaattggga acatgctaaa   6420
tacaaatggt atcttaagga actccaggat ggcattgggc agcggcaaac tgttgtcaga   6480
acattgaatg caactgggga agaaataatt cagcaatcct caaaaacaga tgccagtatt   6540
ctacaggaaa aattgggaag cctgaatctg cggtggcagg aggtctgcaa acagctgtca   6600
gacagaaaaa agaggctaga agaacaaaag aatatcttgt cagaatttca aagagattta   6660
aatgaatttg ttttatggtt ggaggaagca gataacattg ctagtatccc acttgaacct   6720
ggaaaagagc agcaactaaa agaaaagctt gagcaagtca agttactggt ggaagagttg   6780
cccctgcgcc agggaattct caaacaatta aatgaaactg gaggacccgt gcttgtaagt   6840
gctcccataa gcccagaaga gcaagataaa cttgaaaata agctcaagca gacaaatctc   6900
cagtggataa aggtttccag agctttacct gagaaacaag gagaaattga agctcaaata   6960
aaagaccttg ggcagcttga aaaaaagctt gaagaccttg aagagcagtt aaatcatctg   7020
ctgctgtggt tatctcctat taggaatcag ttggaaattt ataaccaacc aaaccaagaa   7080
ggaccatttg acgttcagga aactgaaata gcagttcaag ctaaacaacc ggatgtggaa   7140
gagattttgt ctaaagggca gcatttgtac aaggaaaaac cagccactca gccagtgaag   7200
aggaagttag aagatctgag ctctgagtgg aaggcggtaa accgtttact tcaagagctg   7260
agggcaaagc agcctgacct agctcctgga ctgaccacta ttggagcctc tcctactcag   7320
actgttactc tggtgacaca acctgtggtt actaaggaaa ctgccatctc caaactagaa   7380
atgccatctt ccttgatgtt ggaggtacct gctctggcag atttcaaccg ggcttggaca   7440
gaacttaccg actggctttc tctgcttgat caagttataa aatcacagag ggtgatggtg   7500
ggtgaccttg aggatatcaa cgagatgatc atcaagcaga aggcaacaat gcaggatttg   7560
gaacagaggc gtccccagtt ggaagaactc attaccgctg cccaaaattt gaaaaacaag   7620
accagcaatc aagaggctag aacaatcatt acggatcgaa ttgaaagaat tcagaatcag   7680
tgggatgaag tacaagaaca ccttcagaac cggaggcaac agttgaatga aatgttaaag   7740
gattcaacac aatggctgga agctaaggaa gaagctgagc aggtcttagg acaggccaga   7800
gccaagcttg agtcatggaa ggagggtccc tatacagtag atgcaatcca aaagaaaatc   7860
acagaaacca agcagttggc caaagacctc cgccagtggc agacaaatgt agatgtggca   7920
aatgacttgg ccctgaaact tctccgggat tattctgcag atgataccag aaaagtccac   7980
atgataacag agaatatcaa tgcctcttgg agaagcattc ataaaagggt gagtgagcga   8040
gaggctgctt tggaagaaac tcatagatta ctgcaacagt tcccccctgga cctggaaaag   8100
tttcttgcct ggcttacaga agctgaaaca actgccaatg tcctacagga tgctacccgt   8160
aaggaaaggc tcctagaaga ctccaaggga gtaaaagagc tgatgaaaca atggcaagac   8220
ctccaaggtg aaattgaagc tcacacagat gtttatcaca acctggatga aaacagccaa   8280
aaaatcctga gatccctgga aggttccgat gatgcagtcc tgttacaaag acgtttggat   8340
aacatgaact tcaagtggag tgaacttcgg aaaaagtctc tcaacattag gtcccatttg   8400
gaagccagtt ctgaccagtg gaagcgtctg cacctttctc tgcaggaact tctggtgtgg   8460
```

-continued ctacagctga aagatgatga attaagccgg caggcaccta ttggaggcga ctttccagca 8520
gttcagaagc agaacgatgt acatagggcc ttcaagaggg aattgaaaac taaagaacct 8580
gtaatcatga gtactcttga gactgtacga atatttctga cagagcagcc tttggaagga 8640
ctagagaaac tctaccagga gcccagagag ctgcctcctg aggagagagc ccagaatgtc 8700
actcggcttc tacgaaagca ggctgaggag gtcaatactg agtgggaaaa attgaacctg 8760
cactccgctg actggcagag aaaaatagat gagacccttg aaagactcca ggaacttcaa 8820
gaggccacgg atgagctgga cctcaagctg cgccaagctg aggtgatcaa gggatcctgg 8880
cagcccgtgg gcgatctcct cattgactct ctccaagatc acctcgagaa agtcaaggca 8940
cttcgaggag aaattgcgcc tctgaaagag aacgtgagcc acgtcaatga ccttgctcgc 9000
cagcttacca ctttgggcat tcagctctca ccgtataacc tcagcactct ggaagacctg 9060
aacaccagat ggaagcttct gcaggtggcc gtcgaggacc gagtcaggca gctgcatgaa 9120
gcccacaggg actttggtcc agcatctcag cactttcttt ccacgtctgt ccagggtccc 9180
tgggagagag ccatctcgcc aaacaaagtg ccctactata tcaaccacga gactcaaaca 9240
acttgctggg accatcccaa aatgacagag ctctaccagt ctttagctga cctgaataat 9300
gtcagattct cagcttatag gactgccatg aaactccgaa gactgcagaa ggccctttgc 9360
ttggatctct tgagcctgtc agctgcatgt gatgccttgg accagcacaa cctcaagcaa 9420
aatgaccagc ccatggatat cctgcagatt attaattgtt tgaccactat ttatgaccgc 9480
ctggagcaag agcacaacaa tttggtcaac gtccctctct gcgtggatat gtgtctgaac 9540
tggctgctga atgtttatga tacgggacga acagggagga tccgtgtcct gtcttttaaa 9600
actggcatca tttccctgtg taaagcacat ttggaagaca agtacagata ccttttcaag 9660
caagtggcaa gttcaacagg attttgtgac cagcgcaggc tgggcctcct tctgcatgat 9720
tctatccaaa ttccaagaca gttgggtgaa gttgcatcct ttgggggcag taacattgag 9780
ccaagtgtcc ggagctgctt ccaatttgct aataataagc cagagatcga agcggccctc 9840
ttcctagact ggatgagact ggaaccccag tccatggtgt ggctgcccgt cctgcacaga 9900
gtggctgctg cagaaactgc caagcatcag gccaaatgta acatctgcaa agagtgtcca 9960
atcattggat tcaggtacag gagtctaaag cactttaatt atgacatctg ccaaagctgc 10020 ttttttctg gtcgagttgc aaaaggccat aaaatgcact atcccatggt ggaatattgc 10080
actccgacta catcaggaga agatgttcga gactttgcca aggtactaaa aaacaaattt 10140
cgaaccaaaa ggtattttgc gaagcatccc cgaatgggct acctgccagt gcagactgtc 10200
ttagaggggg acaacatgga aactcccgtt actctgatca acttctggcc agtagattct 10260
gcgcctgcct cgtcccctca gctttcacac gatgatactc attcacgcat tgaacattat 10320
gctagcaggc tagcagaaat ggaaaacagc aatggatctt atctaaatga tagcatctct 10380
cctaatgaga gcatagatga tgaacatttg ttaatccagc attactgcca aagtttgaac 10440
caggactccc ccctgagcca gcctcgtagt cctgcccaga tcttgatttc cttagagagt 10500
gaggaaagag gggagctaga gagaatccta gcagatcttg aggaagaaaa caggaatctg 10560
caagcagaat atgaccgtct aaagcagcag cacgaacata aaggcctgtc cccactgccg 10620
tcccctcctg aaatgatgcc cacctctccc cagagtcccc gggatgctga gctcattgct 10680
gaggccaagc tactgcgtca acacaaaggc cgcctggaag ccaggatgca aatcctggaa 10740
gaccacaata aacagctgga gtcacagtta cacaggctaa ggcagctgct ggagcaaccc 10800

-continued

```
caggcagagg ccaaagtgaa tggcacaacg gtgtcctctc cttctacctc tctacagagg  10860

tccgacagca gtcagcctat gctgctccga gtggttggca gtcaaacttc ggactccatg  10920

ggtgaggaag atcttctcag tcctccccag gacacaagca cagggttaga ggaggtgatg  10980

gagcaactca acaactcctt ccctagttca agaggaagaa atacccctgg aaagccaatg  11040

agagaggaca caatgtag                                                11058
```